United States Patent
Cho et al.

(10) Patent No.: US 9,888,879 B1
(45) Date of Patent: Feb. 13, 2018

(54) METHOD AND SYSTEM FOR ESTIMATING FRACTIONAL FAT CONTENT OF AN OBJECT

(71) Applicant: ENDRA Life Sciences Inc., Ann Arbor, MI (US)

(72) Inventors: Jang Hwan Cho, Ann Arbor, MI (US); Michael M. Thornton, London (CA)

(73) Assignee: ENDRA LIFE SCIENCES INC., Ann Arbor, MI (US)

( * ) Notice: Subject to any disclaimer, the term of this patent is extended or adjusted under 35 U.S.C. 154(b) by 0 days.

(21) Appl. No.: 15/666,535

(22) Filed: Aug. 1, 2017

(51) Int. Cl.
*A61B 5/00* (2006.01)
*A61B 8/08* (2006.01)
*A61B 8/00* (2006.01)

(52) U.S. Cl.
CPC .......... *A61B 5/4872* (2013.01); *A61B 5/0035* (2013.01); *A61B 5/0095* (2013.01); *A61B 5/4244* (2013.01); *A61B 5/7246* (2013.01); *A61B 5/7485* (2013.01); *A61B 8/0858* (2013.01); *A61B 8/4416* (2013.01); *A61B 8/469* (2013.01); *A61B 8/5223* (2013.01); *A61B 8/5261* (2013.01)

(58) Field of Classification Search
CPC ... A61B 5/4872; A61B 5/0035; A61B 5/0095; A61B 5/4244; A61B 5/7246; A61B 5/7485; A61B 8/0858; A61B 8/4416; A61B 8/469; A61B 8/5223; A61B 8/5261
See application file for complete search history.

(56) References Cited

U.S. PATENT DOCUMENTS

| | | | |
|---|---|---|---|
| 4,385,634 | A | 5/1983 | Bowen |
| 5,713,356 | A | 2/1998 | Kruger |
| 9,706,977 | B2 | 7/2017 | Manohar et al. |
| 2012/0197117 | A1 | 8/2012 | Picot et al. |

OTHER PUBLICATIONS

Xie et al., Adaptive and Robust Methods of Reconstruction (ARMOR) for Thermoacoustic Tomography, IEEE Transactions on Biomedical Engineering, vol. 55, No. 12, Dec. 2008.*

(Continued)

*Primary Examiner* — Bo J Peng
(74) *Attorney, Agent, or Firm* — Stanley E. Jelic

(57) ABSTRACT

A method and system for estimating fractional fat content of an object of interest. An energy emitter is used to direct an energy signal with an energy signal electric field strength toward the region of interest, wherein the region of interest has an object of interest, a reference, and a boundary between the object of interest and the reference. Next, a thermoacoustic or ultrasonic transducer is used to receive a thermoacoustic bipolar signal from the boundary, wherein the thermoacoustic bipolar signal is induced by the energy signal. Finally, a machine is used to accept data from the energy emitter and thermoacoustic or ultrasonic transducer, correlate the thermoacoustic bipolar signal to an electric field strength of the reference at the boundary to generate a corrected thermoacoustic bipolar signal at the boundary, and calculate a fat concentration of the object of interest as a function of the corrected thermoacoustic bipolar signal at the boundary.

19 Claims, 15 Drawing Sheets

(56) References Cited

OTHER PUBLICATIONS

Bu et al., Model-Based Reconstruction IntegratedWith Fluence Compensation for Photoacoustic Tomography, IEEE Transactions on Biomedical Engineering, vol. 59, No. 5, May 2012.*

S. B. Reeder and C. Sirlin, "Quantification of liver fat with magnetic resonance imaging," Magn Reson Imaging Clin N Am vol. 18, No. 3, pp. 337-357, Aug. 2010.

M. P. Andre et al., "Accurate diagnosis of nonalcoholic fatty liver disease in human participants via quantitative ultrasound", 2014 IEEE International Ultrasonics Symposium, 204, pp. 2375-2377, 2014.

O. W. Hamer et al., "Fatty liver: Imaging patterns and pitfalls", Radiographics, vol. 26, No. 6, pp. 1637-1653, 2006.

D. A. Sass, P. Cang, and K. B. Chopra, "Nonalcoholic fatty liver disease: a clinical review," Dig. Dis. Sci., vol. 50, No. 1, pp. 171-180, Jan. 2005.

M. F. Xia et al., "Standardized ultrasound hepatic/renal ratio and hepatic attenuation rate to quantify liver fat content: an improvement method", Obesity, vol. 20, No. 2, pp. 444-452, 2012.

D. R. Bauer et al., "Spectroscopic thermoacoustic imaging of water and fat composition," Appl. Phys. Lett., vol. 101, 2012.

X. Wang et al., "Microwave-induced thermoacoustic imaging model for potential breast cancer detection," IEEE Trans. Biomed. Eng., vol. 59, No. 10, pp. 2782-2791, Oct. 2012.

T. J. Allen et al., "Spectroscopic photoacoustic imaging of lipid-rich plaques in the human aorta in the 740 to 1400 nm wavelength range", J. Biomed. Opt., vol. 17, No. 6, Jun. 2012.

L. Pan et al., "Differentiating fatty and non-fatty tissue using photoacoustic imaging," Proc. of SPIE vol. 8943, 2014.

G. Xu et al., "Functional Pitch of a Liver: Fatty Liver Disease Diagnosis with Photoacoustic Spectrum Analysis," Proc. of SPIE vol. 8943, 2014.

C. Tian et al., "Imaging and sensing based on dual-pulse nonlinear photoacoustic contrast: a preliminary study on fatty liver," Optics Letters, vol. 40, No. 10, pp. 2253-2256, May 2015.

G. Ku and L. V. Wang, "Scanning thermoacoustic tomography in biological tissue," Med. Phys., vol. 27, No. 5, pp. 1195-202, May 2000.

G. J. Diebold and T. Sun, "Properties of photoacoustic waves in one, two, and three dimensions," Acta. Acust. united. Ac., vol. 80, No. 4, pp. 339-351, Jul. 1994.

X. L. Dean-Ben, "On the link between the speckle free nature of optoacoustics and visibility of structures in limited-view tomography," Photoacoustics, vol. 4, No. 4, pp. 133-140, Jul. 2016.

C. Gabriel et al., "The dielectric properties of biological tissues: I. Literature survey," Med. Phys., vol. 41, No. 11, pp. 2231-2249, Nov. 1996.

S. Gabriel et al., "The dielectric properties of biological tissues: II. Measurements in the frequency range 10 Hz to 20 GHz," Med. Phys., vol. 41, No. 11, pp. 2251-2269, Nov. 1996.

S. K. Ng et al., "Determination of added fat in meat paste using microwave and millimetre wave techniques," Meat Science, vol. 79, No. 4, pp. 748-756, Aug. 2008.

* cited by examiner

METHOD AND SYSTEM FOR ESTIMATING FRACTIONAL FAT CONTENT OF AN OBJECT

FIELD

This application relates to a method and system for estimating fractional fat content of an object.

BACKGROUND

Hepatic steatosis, also known as fatty liver disease, is a condition where hepatocytes suffer from abnormal intracellular accumulation of fat, mostly in the form of triglycerides (TG). The two main types of hepatic steatosis are alcoholic liver disease (ALD) and non-alcoholic fatty liver disease (NAFLD). NAFLD is the most common cause of chronic liver disease in the United States. Hepatic steatosis can lead to progressive hepatic disease and is a risk factor for cardiovascular disease and diabetes. Liver biopsy with histologic analysis is commonly used for diagnosing and grading a fatty liver. However, due to the invasive nature of liver biopsy with histologic analysis and limitations such as lack of representation of the entire liver, non-invasive assessments based on cross-sectional imaging are being investigated.

Ultrasound imaging has been used for evaluating hepatic steatosis. Ultrasound imaging uses sound waves with frequencies higher than those audible to humans (>20,000 Hz). These sound waves are pulsed into tissue using a probe. The sound waves echo off the tissue. Different tissues reflect different degrees of sound. These echoes are analyzed through signal processing and are further processed using clinical ultrasound reconstruction algorithms to reconstruct ultrasound images for presentation and interpretation by an operator. Many different types of images can be reconstructed using ultrasound imaging. One such type is a B-mode image which displays the acoustic impedance of a two-dimensional cross-section of tissue. Ultrasound imaging, however, suffers from poor repeatability and reproducibility in evaluating hepatic steatosis.

Unenhanced computed tomography (CT) has been used for evaluating hepatic steatosis. Using unenhanced CT, fatty liver can be diagnosed based on its attenuation value and relative relationship with the spleen and blood. However, the sensitivity of unenhanced CT is limited.

Magnetic resonance imaging (MRI) is currently the most accurate and precise non-invasive imaging modality for diagnosing and quantifying hepatic steatosis. MRI data can be processed to estimate proton density fat fraction (PDFF) as a measure of fractional fat content. However, MRI is expensive.

Although techniques for detecting and grading hepatic steatosis have been considered, improvements are desired. It is therefore an object to provide a novel method and system for estimating fractional fat content of an object using thermoacoustic imaging.

SUMMARY

In one embodiment, a method for identifying fat content in a region of interest comprises: directing an energy signal with an energy signal electric field strength toward the region of interest, wherein the region of interest has an object of interest, a reference, and a boundary between the object of interest and the reference; receiving a thermoacoustic bipolar signal from the boundary, wherein the thermoacoustic bipolar signal is induced by the energy signal; correlating the thermoacoustic bipolar signal to an electric field strength of the reference at the boundary to generate a corrected thermoacoustic bipolar signal at the boundary; and calculating a fat concentration of the object of interest as a function of the corrected thermoacoustic bipolar signal at the boundary.

In one embodiment, the thermoacoustic bipolar signal is received by one thermoacoustic or ultrasonic transducer.

In one embodiment, the reference electric field strength at the boundary is derived from an attenuation coefficient of the reference.

In one embodiment, the reference is a subcutaneous fat.

In one embodiment, the method further comprises estimating a thickness of the subcutaneous fat, immediately after the receiving step.

In one embodiment, the reference electric field strength at the boundary is a function of the estimated thickness of the subcutaneous fat and attenuation coefficient of fat.

In one embodiment, the object of interest is a liver and the calculated fat concentration correlates to a hepatic steatosis condition.

In one embodiment, the energy signal is a radio-frequency pulse.

In one embodiment, the energy signal is a visible light.

In one embodiment, the energy signal is an infrared radiation.

In one embodiment, a system configured to identify fat content in a region of interest comprises: an energy emitter configured to direct an energy signal with an energy signal electric field strength toward the region of interest, wherein the region of interest has an object of interest, a reference, and a boundary between the object of interest and the reference; a thermoacoustic or ultrasonic transducer configured to receive a thermoacoustic bipolar signal from the boundary, wherein the thermoacoustic bipolar signal is induced by the energy signal; and a machine configured to accept data from the energy emitter and thermoacoustic or ultrasonic transducer, correlate the thermoacoustic bipolar signal to an electric field strength of the reference at the boundary to generate a corrected thermoacoustic bipolar signal at the boundary, and calculate a fat concentration of the object of interest as a function of the corrected thermoacoustic bipolar signal at the boundary.

BRIEF DESCRIPTION OF THE DRAWINGS

Embodiments will now be described more fully with reference to the accompanying drawings in which.

DETAILED DESCRIPTION OF THE EMBODIMENTS

In the following, a method and system for estimating fractional fat content of an object of interest will be described. Generally, the method comprises obtaining at least one set of thermoacoustic data of a region of interest containing an object of interest and a reference. The electric field strength at a boundary between the object of interest and the at least one reference can be estimated. The fractional fat content of the object of interest is estimated using the electric field strength and the thermoacoustic data. The object of interest is graded using the estimated fractional fat content thereof.

Figure 1:
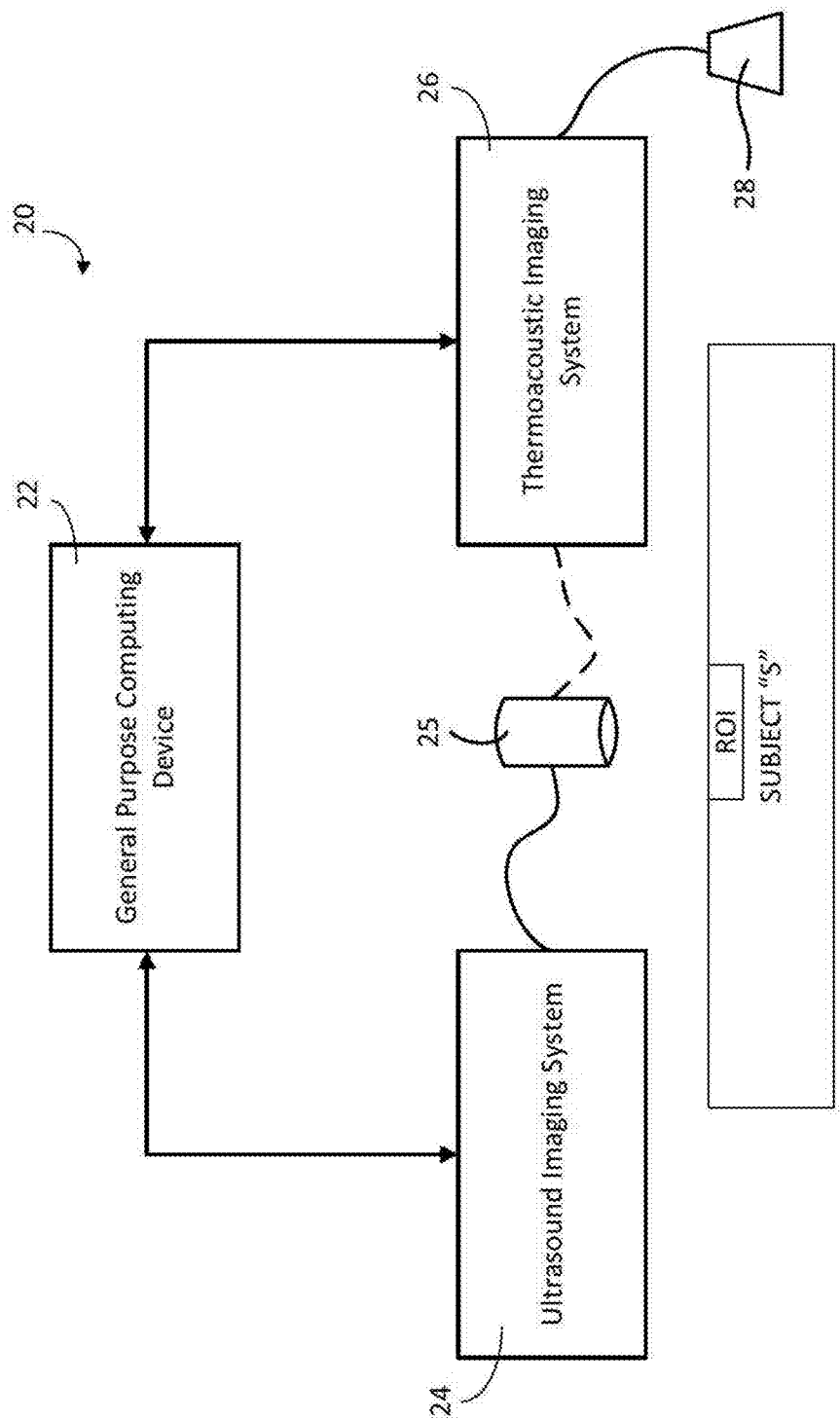
FIG. 1 is a schematic view of an imaging system in accordance with the subject application.

Turning now to FIG. 1, an imaging system is shown and is generally identified by reference numeral 20. As can be seen, in this embodiment the imaging system 20 comprises a computing device 22 communicatively coupled to an ultrasound imaging system 24 and a thermoacoustic imaging system 26. The ultrasound imaging system 24 and thermoacoustic imaging system 26 are configured to obtain ultrasound image data and thermoacoustic data, respectively, of a region of interest (ROI) associated within a subject S.

The computing device 22 in this embodiment is a machine comprising a personal computer or other suitable processing device comprising, for example, a processing unit comprising one or more processors, system memory (volatile and/or non-volatile memory), other non-removable or removable memory (e.g., a hard disk drive, RAM, ROM, EEPROM, CD-ROM, DVD, flash memory, etc.) and a system bus coupling the various computer components to the processing unit. The computing device 22 may also comprise networking capabilities using Ethernet, Wi-Fi, and/or other suitable network format, to enable connection to shared or remote drives, one or more networked computers, or other networked devices. One or more input devices, such as a mouse and a keyboard (not shown) are coupled to the computing device 22 for receiving user input. A display device (not shown), such as a computer screen or monitor, is coupled to the computer device 22 for displaying one or more generated images that are based on ultrasound image data received from the ultrasound imaging system 24 and/or the thermoacoustic data received from thermoacoustic imaging system 26.

The ultrasound imaging system 24 comprises one or more ultrasound transducer arrays 25 configured to emit sound waves into the region of interest ROI of the subject. In this embodiment, the one or more ultrasound transducer arrays 25 are disconnectable from the ultrasound imaging system 24. The sound waves directed into the region of interest ROI of the subject echo off tissue within the region of interest ROI, with different tissues reflecting varying degrees of sound. These echoes are received by the one or more ultrasound transducer arrays 25 and are processed by the ultrasound imaging system 24 before being communicated as ultrasound image data to the computing device 22 for further processing and for presentation and interpretation by an operator. In this embodiment the ultrasound imaging system 24 utilizes B-mode ultrasound imaging techniques assuming a nominal speed of sound of 1,540 m/s.

The thermoacoustic imaging system 26 comprises a radio-frequency (RF) source 28 configured to generate short pulses of RF electromagnetic radiation that are directed into the region of interest ROI of the subject to deliver energy to tissue within the region of interest ROI of the subject. The energy delivered to the tissue induces acoustic pressure waves that are detected by the thermoacoustic imaging system 26 using one or more ultrasound transducer arrays. In this embodiment, the thermoacoustic imaging system 26 makes use of the one or more ultrasound transducer arrays 26 of the ultrasound imaging system 26 by disconnecting the one or more ultrasound transducer arrays 25 of the ultrasound imaging system 24 and connecting them to the thermoacoustic imaging system 26 and as such, coordinate mapping between ultrasound transducer arrays 25 is not required. In this embodiment, the RF source has a frequency between about 10 MHz and 100 GHz and has a pulse duration between about 0.1 nanoseconds and 10 microseconds. Acoustic pressure waves detected by the one or more ultrasound transducer arrays 25 are processed and communicated as thermoacoustic data to the computing device 22 for further processing and for presentation and interpretation by an operator.

In a separate embodiment, the thermoacoustic imaging system 26 could utilize separate thermoacoustic transducers from the ultrasound transducer arrays 25.

Thermoacoustic imaging can be used to contrast between fat and fatty tissues due to their lower electrical conductivity and permittivity in RF compared to other water and ion-rich soft tissues. Fat and fatty tissues also have a lower absorption coefficient compared to soft tissues like muscle. As such, obtaining thermoacoustic data of both fatty and soft tissues results in a bipolar signal at a boundary between the fatty tissue and the soft tissue. The strength of the bipolar signal depends on the relative absorption properties of the fatty tissue and the soft tissue. Further details can be found in the following references: "Scanning thermoacoustic tomography in biological tissue" authored by Ku et al., Med. Phys., vol. 27, no. 5, pp. 1195-202. May 2000; "Microwave-induced thermoacoustic imaging model for potential breast cancer detection" authored by Wang et al., IEEE Trans. Biomed. Eng., vol. 59, no. 10, pp. 2782-01, October 2012; and "IT'IS Database for thermal and electromagnetic parameters of biological tissues" authored by Hasgall et al. Version 3.0, September 2015.

Figure 2:
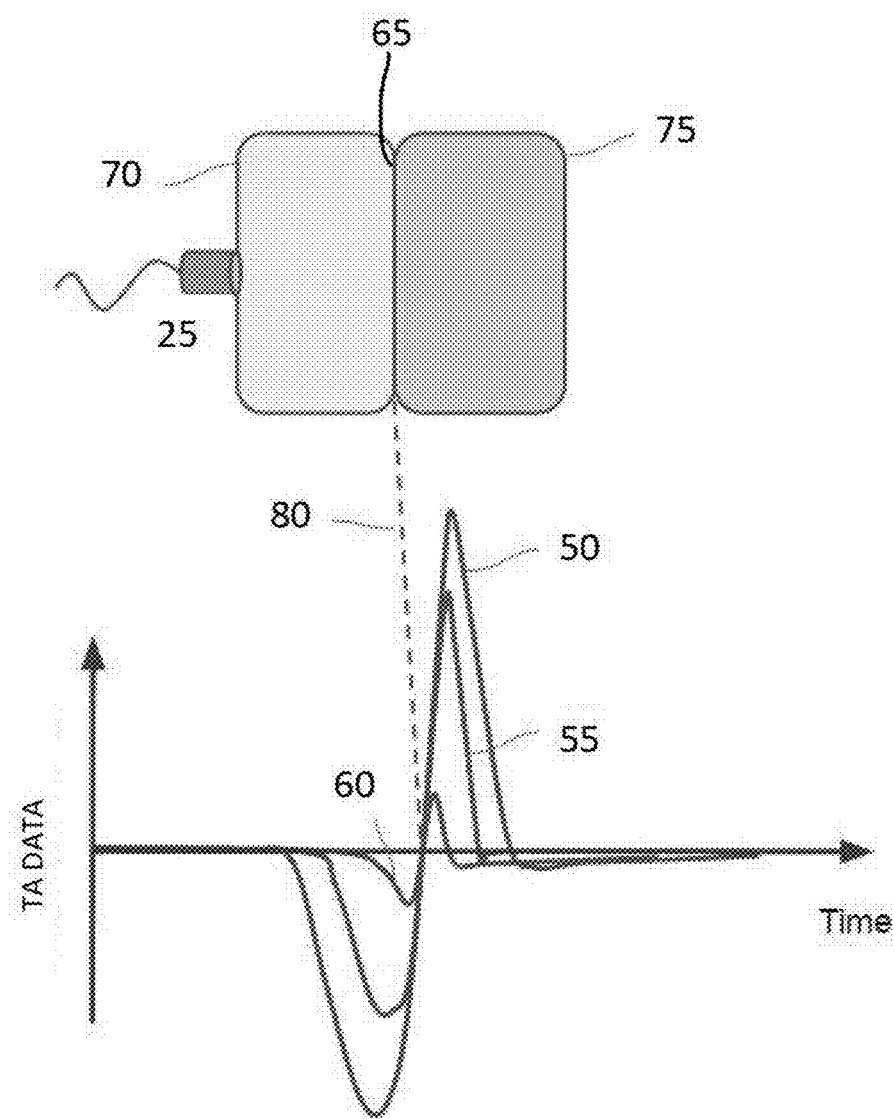
FIG. 2 is a graph showing exemplary bipolar signals obtained by the imaging system of FIG. 1.

Exemplary bipolar signals 50, 55, and 60 are shown in FIG. 2. The bipolar signals 50, 55, and 60 represent thermoacoustic data obtained at a boundary 65 between fatty tissue 70 and lean tissue 75. The dashed line 80 indicates a time point corresponding to the boundary 85. The peak-to-peak value of each bipolar signal 50, 65, and 60 is proportional to a difference in absorption coefficient between the fatty tissue 70 and lean tissue 75. As such, thermoacoustic data associated with a boundary between tissue having no fat (such as a kidney) and tissue having a high fraction fat content (such as a fatty liver) results in bipolar signal 50. Thermoacoustic data associated with a boundary between tissue having no fat (such as a kidney) and tissue having a medium fractional fat content (such as an unhealthy liver) results in bipolar signal 55, Thermoacoustic data associated with a boundary between tissue having no fat (such as a kidney) and tissue having a low fractional fat content (such as a healthy liver) results in bipolar signal 60.

Different tissues have characteristic dielectric properties at a given frequency. The dielectric properties of tissue determines how much energy is absorbed by the tissue. An electric field transmitted through the tissue is attenuated, and the amount of attenuation is determined by both dielectric and physical properties of the tissue. Generally, compared to normal tissue, fatty tissue absorbs less energy and thus attenuates less electric field. Knowing these properties, the amount of attenuation can be estimated. Further details can be found in the reference entitled "Determination of added fat in meat paste using microwave and millimeter wave techniques" authored by Ng et al., *Meat Science*, vol. 79, no. 4, pp. 748-56, August 2008.

Figure 3:
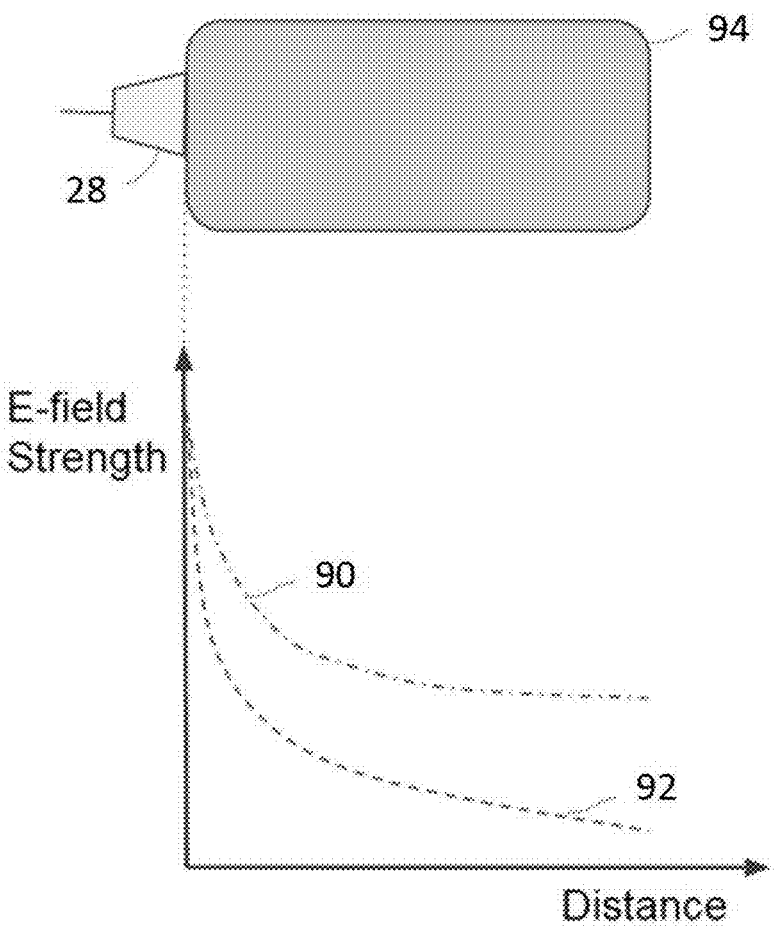
FIG. 3 is a graph showing exemplary electric field strength attenuation curves obtained by the imaging system of FIG. 1.

FIG. 3 shows electric field strength attenuation curves 90 and 92 in tissue 94 as a function of distance from the RF source 28 of the thermoacoustic imaging system 26. Each electric field strength attenuation curve 90 and 92 corresponds to fatty tissue, each of which has a different fat concentration. The fatty tissue associated with electric field strength curve 90 has a higher fat concentration than the fatty tissue associated with electric field strength curve 92.

The imaging system 20 exploits the relationship between the dielectric properties and fractional fat content to estimate fractional fat content of an object of interest. In this embodiment, the imaging system 20 performs a method for grading an object of interest based on the fractional fat content thereof, as will now be described with reference to FIG. 4.

The method begins by directing an energy signal with an energy signal electric field strength toward the region of interest, wherein the region of interest has an object of interest, a reference, and a boundary between the object of interest and the reference (step 401). In this embodiment, the region of interest is located using the ultrasound imaging system 24. Specifically, ultrasound image data obtained by the ultrasound imaging system 24 is communicated to the computing device 22. The ultrasound image data is processed by the computing device 22 and a reconstructed ultrasound image is presented on the display device. The operator moves the one or more ultrasound transducer arrays on the subject's body until the region of interest is located. In one embodiment, when locating the region of interest, the computing device 22 overlays information associated with the angle of the axial axis (or ultrasound transducer array beam axis) of the one or more transducer arrays overtop of the reconstructed ultrasound image on the display device. The information is used to provide feedback to the operator to ensure the axial axis of the one or more transducer arrays are generally perpendicular to a boundary between the object of interest and the reference.

Figure 5:
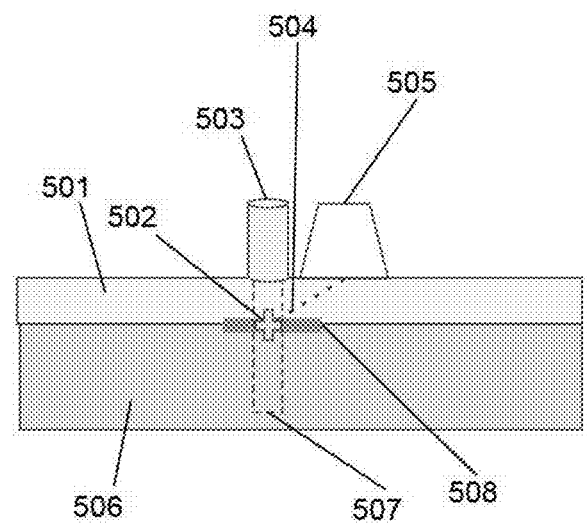
FIG. 5 is an exemplary region of interest containing an object of interest and a reference.

An exemplary region of interest encompasses a reference (subcutaneous skin) 501 and object of interest (liver tissue) 506 as shown in FIG. 5. A boundary region 508 between the reference 801 and object of interest 506 contains a boundary location 502. Also shown in FIG. 5 is an energy emitter 506 configured to direct an energy signal 604 through the reference 501 to the boundary location 502. A box 507 is shown running parallel to a corresponding thermoacoustic or ultrasonic transducer 503.

In step 402, we receive a thermoacoustic bipolar signal with the thermoacoustic or ultrasonic transducer 503 from the boundary location 502, wherein the thermoacoustic bipolar signal is induced by the energy signal 504. In this embodiment, the boundary location 602 is identified by the operator using an input device such as a mouse coupled to the computing device 22. Specifically, a box 507 is one embodiment of a shape with at least a portion of the object of interest 506, at least a portion of the reference 601 and the boundary 502 between the object of interest 506 and the reference 601. The box is typically rectangular with a long axis (parallel to the long sides) and a short axis (parallel to the short sides). The computing device 22 provides feedback to the user via the display device to indicate the approximate angle between the long axis of the box 507 and the boundary 502 to ensure the long axis of the box 507 is generally perpendicular to the boundary 502.

As will be appreciated, an ultrasound image grid is defined by size, its position relative to the region of interest and a unit-cell (voxel) size. The ultrasound image grid and position are defined such that boundary is enclosed within the grid. From the ultrasound image grid, a thermoacoustic measurement grid is constructed to ensure registration of the thermoacoustic image location to the ultrasound image coordinates. In this embodiment, since the thermoacoustic data is obtained using one of the ultrasound transducer arrays used for obtaining the ultrasound image data and, the thermoacoustic measurement grid is easily constructed. Specifically, the thermoacoustic measurement grid is equal to the ultrasound image grid.

Figure 4:
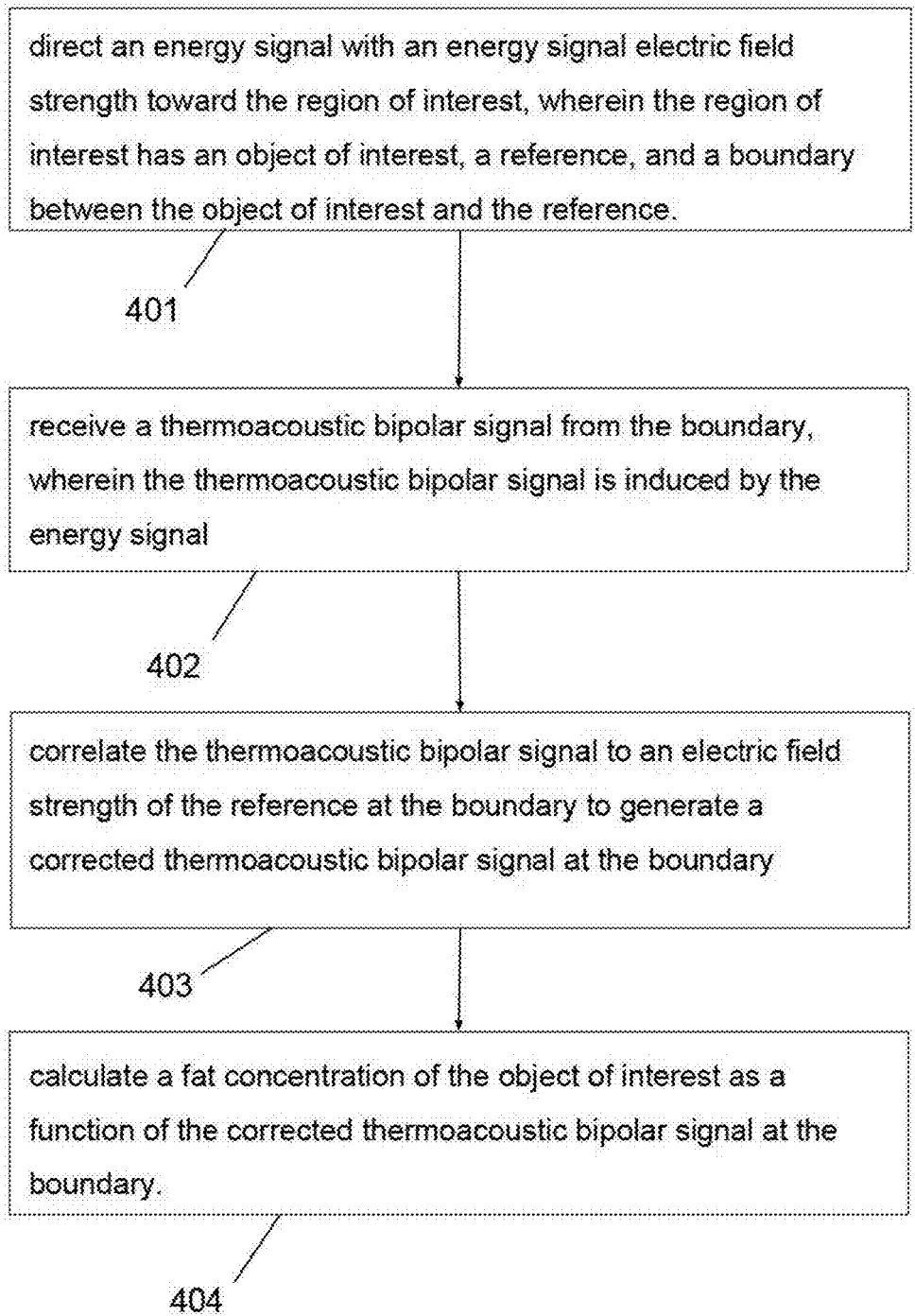
FIG. 4 is a flowchart of a method for calculating a fat concentration of an object of interest.

FIG. 4 further shows the steps of correlating the thermoacoustic bipolar signal to an electric field strength of the reference at the boundary to generate a corrected thermoacoustic bipolar signal at the boundary 403 and calculating a fat concentration of the object of interest as a function of the corrected thermoacoustic bipolar signal at the boundary and the energy signal electric field strength 404.

Using the electric field strength at the boundary, the fractional fat content of the object of interest is estimated. To estimate the fractional fat content of the object of interest using the electric field strength, a number of equations are utilized. As is known, the thermoacoustic pressure produced by a heat source H(r, t) obeys the following equation:

$$\nabla^2 p(\bar{r}, t) - \frac{1}{c^2} \frac{\partial^2}{\partial t^2} p(\bar{r}, t) = -\frac{\beta}{C_p} \frac{\partial}{\partial t} H(\bar{r}, t) \tag{1}$$

where $\bar{r}$ is the spatial position vector, $\beta$ is the isobaric volume expansion coefficient, c is the sound speed and $C_p$ is the specific heat capacity. Solving equation 1 with respect to the thermoacoustic pressure yields the following forward problem:

$$p(\bar{r}, t) = \frac{\beta}{4\pi C_p} \iiint \frac{\partial \bar{r}}{|\bar{r} - \bar{r}'|} \frac{\partial H(\bar{r}', t')}{\partial t'} \bigg|_{t' = t - \frac{r'}{c}} \tag{2}$$

The heat source is modeled as the product of two factors: the spatial distribution of energy absorption $A(\bar{r})$, which is the characteristics of the object being imaged, and the temporal irradiation function I(t). Since the ultrasound transducer array has a finite bandwidth, the recorded thermoacoustic measurements $p_d(\bar{r}, t)$ are the convolution of induced pressure $p(\bar{r}, t)$ and the impulse response of the ultrasound transducer array h(t) as set out in equation 3:

$$p_d(\bar{r},t) = p(\bar{r},t) * h(t) \tag{3}$$

where $*_t$ denotes a one-dimensional (1D) temporal convolution.

As will be appreciated, for conventional thermoacoustic imaging, the goal is to recover the spatial absorption distribution A(r) by inverting the forward problem. The irradiation function is modeled as a temporal function that is uniform throughout the field at a given time point.

Due to the limited bandwidth of the ultrasonic transducer array used to receive thermoacoustic data, accurately recovering the absorption distribution is not trivial. As such, extracting quantitative information such as fractional fat content of an object of interest from thermoacoustic data requires sophisticated methods beyond conventional reconstruction methods.

When the object of interest is heated with an RF radiation pulse, the power deposition per unit volume is expressed as:

$$A(\bar{r}) = \omega \epsilon_0 \epsilon_r'' E^2(\bar{r}) \tag{4}$$

where $\omega$ is the radian frequency, $\epsilon_0$ is the vacuum permittivity, $\epsilon_r''$ is the relative permittivity of the tissue and $E(\bar{r})$ is the electric field strength. The strength of thermoacoustic data obtained from a tissue is the product of the deposited energy and the Grünelsen parameter of the tissue, $\Gamma$:

$$S(\bar{r}) = \Gamma A(\bar{r}) = \Gamma \omega \epsilon_0 \epsilon_r'' E^2(\bar{r}) \tag{5}$$

As will be appreciated, because of the impulse response characteristic of the ultrasonic transducer, the recorded thermoacoustic data exhibits bipolar signals at a boundary between two different tissues. The strength of the bipolar thermoacoustic data is defined as a distance between two peaks of the bipolar signal. As will be appreciated, in other embodiments the metric may also incorporate other information such as for example a width of the bimodal signal.

Within dielectric lossy medium, the electric field strength is attenuated as it propagates through the medium. The amount of attenuation is determined by various factors such as characteristics of the medium (object) and design of the applicator. Spatial distribution of the electric field can be written as follows $$E(\bar{r}) = E_0 E_A(\bar{r}) \tag{6}$$

where $E_0$ denotes the maximum electric field strength forward to the medium and $E_A(\bar{r})$ describes the attenuation of the electric field over the given space. For a simple 1D case, the attenuation function may have the following exponential form:

$$E_A(d) = e^{-\eta d} \tag{7}$$

where $\eta$ is the electric field absorption coefficient and d is the distance from the applicator.

In this embodiment, equation 5 is used as a model to infer fractional fat content from the thermoacoustic data. As mentioned previously, thermoacoustic data obtained from the boundary between the object of interest and the reference is a bipolar signal. The strength of the bipolar signal represents the absorption property difference between the object of interest and the reference. Further, the phase of the thermoacoustic data at the boundary indicates which tissue (object of interest or the reference) has a higher or lower absorption coefficient. The strength of the thermoacoustic signal measured at the boundary location, $r_1$, is expressed in equation 8:

$$S_1 = (\Gamma_1 \epsilon_{r,1}'' - \Gamma_2 \epsilon_{r,2}'') \omega \epsilon_0 E_1^2 \tag{8}$$

where subscripts 1 and 2 denote two different tissues located on each side of the boundary location, $r_1$, and $E_1$ denotes the incident electric field strength at the boundary location.

As shown in equation 8, the strength of the acquired thermoacoustic data is determined by several tissue properties and the strength of the electric field.

Since the properties of the reference are known, to estimate the fractional fat content of the object of interest, only the strength of the electric field at the boundary is required. Put another way, since tissue with a higher fractional fat content will have different dielectric and thermal properties than lean (no fat content) tissue, the fractional fat content of the region of interest of a tissue is deduced.

We can estimate the incident electric field, $E_1$, at the boundary location 502 (going from reference to object of interest) from the following equation, using Eq. (6):

$$E_1 = E_0 e^{-\eta_{ref} d_{ref}} \tag{9}$$

where $E_0$ is the electric field strength at the start of the reference, $\eta_{ref}$ is the attenuation coefficient of the reference, $d_{ref}$ is the thickness of the reference. Electric field strength, $E_0$, can be modeled (for example, via finite-difference time domain (FDTD) method) and inferred from measurements at the skin.

The thermoacoustic signal strength at the boundary location can be written as follows (from equation 8 and 9):

$$S_1 = (\Gamma_{obj} \epsilon_{r,obj}'' - \Gamma_{ref} \epsilon_{r,ref}'') \omega \epsilon_0 E_1^2 = (\theta_{obj} \epsilon_{r,obj}'' - \Gamma_{ref} \epsilon_{r,ref}'') \omega \epsilon_0 E_0^2 e^{-2\eta_{ref} d_{ref}} \tag{10}$$

Now, the products of unknown quantities of liver can be calculated as follows:

$$\kappa_{obj} \equiv \Gamma_{obj} \epsilon_{r,obj}'' = \frac{S_l}{\omega \epsilon_0 E_0^2 e^{-2\eta_{ref} d_{ref}}} + \Gamma_{ref} \epsilon_0 \epsilon_{r,r,ref}'' \tag{11}$$

For different fat content, the new property, $\kappa_{obj}$, can be tabulated from models and experiments. Each components of $\kappa_{obj}$ can be either measured or modeled for different fat content.

Figure 7:
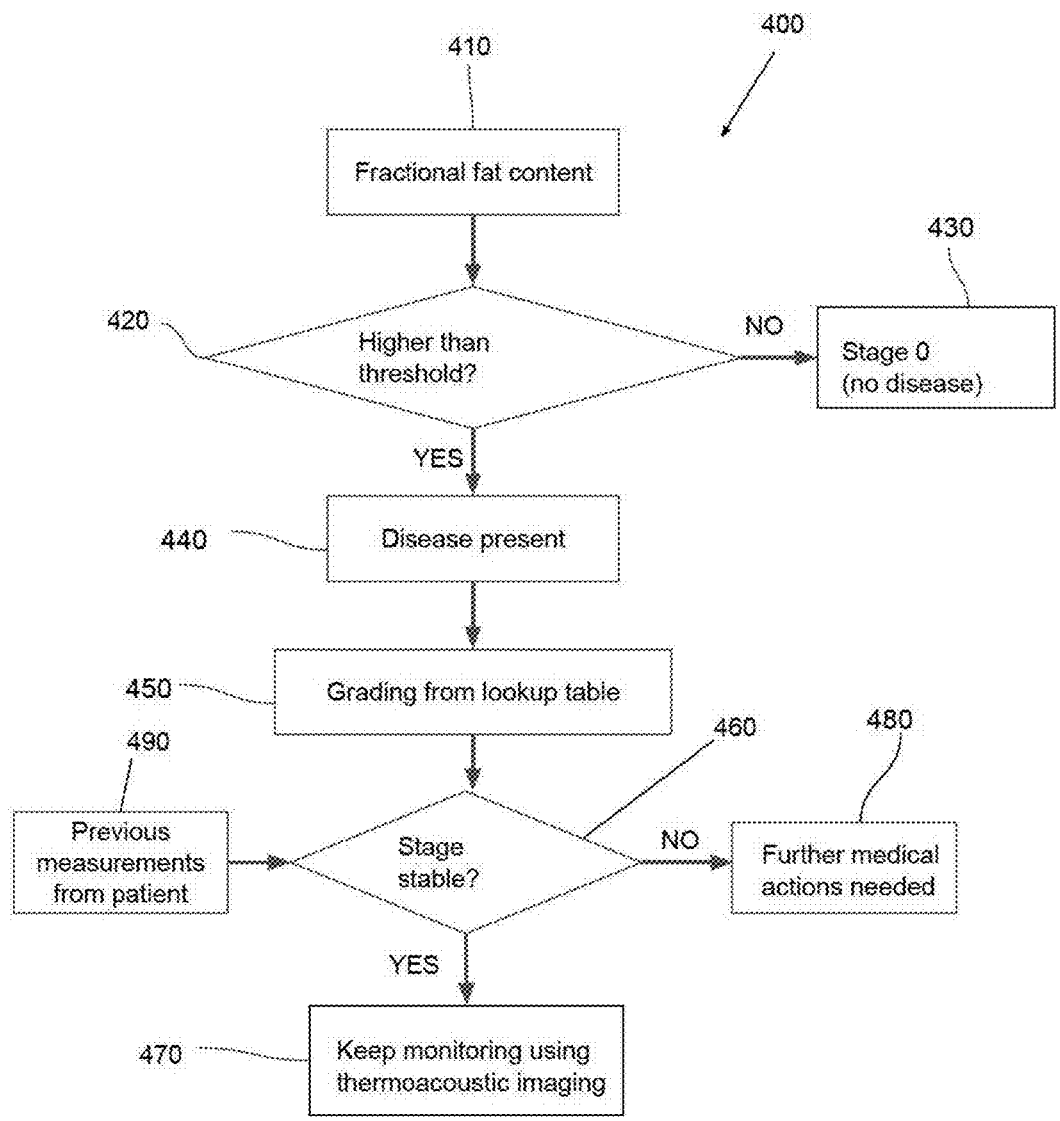
FIG. 7 is a flowchart showing steps for grading an object of interest.

In one embodiment, the object of interest is graded according to a method 400 shown in FIG. 7. During the method, the estimated fractional fat content (step 410) is compared to a threshold (step 420). In this embodiment, the threshold is for fatty liver disease and is set at a fractional fat content of 5%. Specifics of the threshold for fatty liver disease are outlined in "Magnetic resonance imaging and liver histology as biomarkers of hepatic steatosis in children with non-alcoholic fatty liver disease," authored by Schwimmer, *Hepatology*, vol. 61, pp. 1887-1895, 2015.

If the estimated fractional fat content is less than the threshold, it is determined that the subject does not have a disease and thus the object of interest is graded as a zero (0) (step 430). If the estimated fractional fat content is higher than the threshold, it is determined that a disease such as steatosis is present (step 440). The object of interest is in turn graded as a one (1), two (2) or three (3) by comparing the estimated fractional fat content to known tabulated values (step 450). In this embodiment, the known tabulated values are outlined in "Non-alcoholic steatohepatitis: A proposal for grading and staging the histological lesions," authored by Brunt et al., Am. J. Gastroenterol., vol. 94, no. 9, pp. 2467-2474, September 1999.

Specifically, in this embodiment, the object of interest is graded as a one (1) if the estimated fractional fat content is between 5% and 33%. The object of interest is graded as a two (2) if the estimated fractional fat content is between 34% and 66%. The object of interest is graded as a three (3) if the estimated fractional fat content is greater than 66%.

The grade of the object of interest is then compared to previous grades obtained for the subject (if available) (step 460). If the grade of the object of interest has not changed, the object of interest is deemed stable and the subject is released (step 470). If the grade of the object of interest has changed, further medical actions are deemed to be required (step 480).

In an embodiment, it is assumed that a subject having a high fractional fat content of an object of interest, such as the liver, will have a thick layer of subcutaneous fat. The subcutaneous fat may be used as the reference to estimate the fractional fat content of the liver. In this embodiment, the electric field strength at the boundary between the object of interest (liver) and the reference (subcutaneous fat) is estimated using the subcutaneous fat. In this embodiment, ultrasound image data is processed by the computing device 22 to estimate the thickness of the subcutaneous fat. Using the thickness of the subcutaneous fat, the set of thermoacoustic data is analyzed to determine the electric field strength after the subcutaneous fat.

Although in embodiments described above the computing device 22 provides feedback to the user via the display device to indicate the approximate angle between the box and the boundary to ensure the box is generally perpendicular to the boundary, those skilled in the art will appreciate that additions or alternatives are available. For example, the thermoacoustic data may be adjusted to correct for embodiments where the box is not perpendicular to the boundary.

Figure 8:
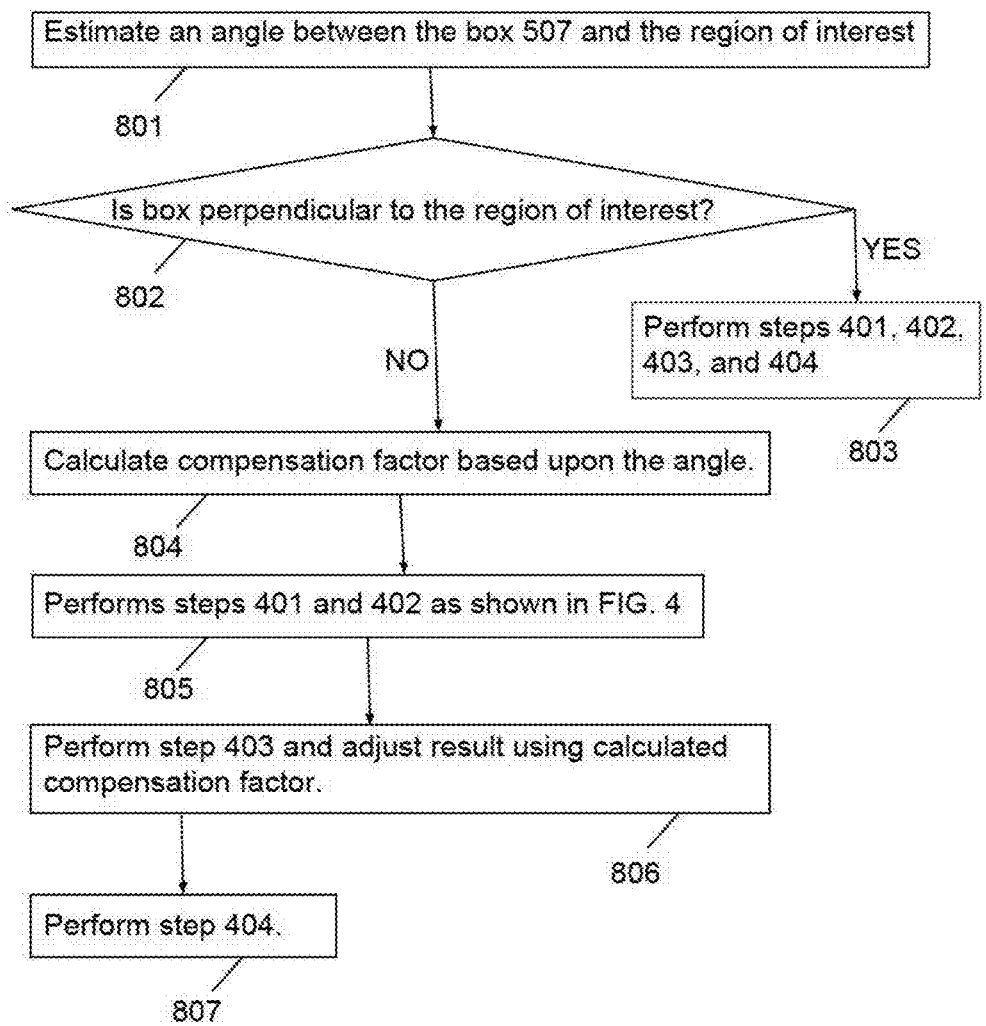
FIG. 8 is a flowchart of an thermoacoustic data adjustment.

In one embodiment, a thermoacoustic data adjustment may be used as shown in FIG. 8. In this embodiment: estimate an angle between the box 507 and the region of interest (step 801); determine if the box is perpendicular to the region of interest (step 802); if yes, perform steps 401, 402, 403, and 404 (step 803); if no, calculate compensation factor based upon the angle (step 804); perform steps 401 and 402 (step 805); perform step 403 and adjust result using calculated compensation factor (step 806); and perform step 404 (step 807).

Figure 9:
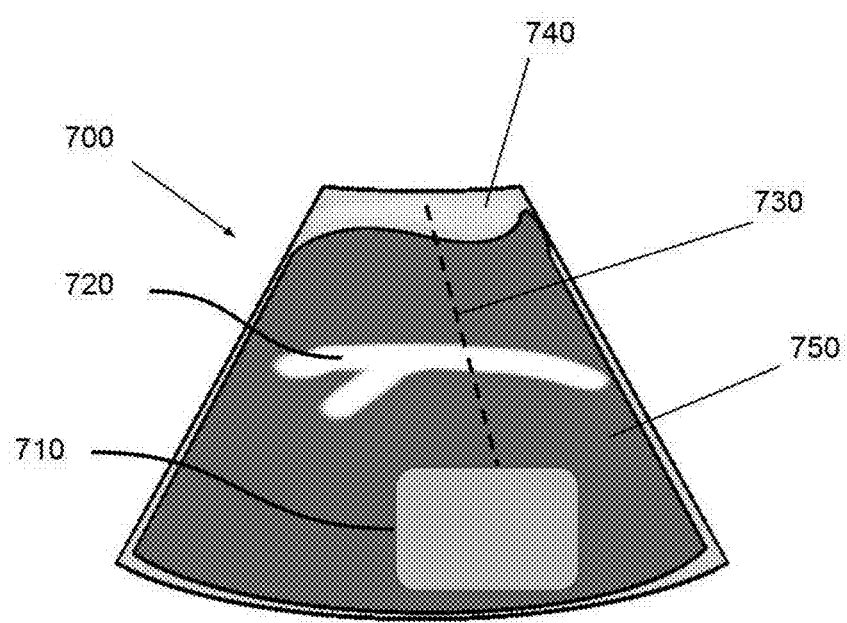
FIG. 9 is another exemplary region of interest containing an object of interest and a reference.

Although in embodiments described above, the reference is described as being adjacent to the object of interest, those skilled in the art will appreciate that other types of tissue may be used. For example, in another embodiment one or more blood vessels may be used as a reference. Also, there can be more than one reference. In this embodiment, the reconstructed ultrasound image displayed on the display device may be used by the operator to identify and select the one or more blood vessels. An example is shown in FIG. 9. As can be seen, a region of interest 700 includes the object of interest 710. The region of interest 700 also includes a reference 720 which in this example is a blood vessel. Boundaries are identified by placing a line 730 that passes through the references (720, 740, and 760) and the object of interest 710.

In some embodiments, thermoacoustic image data may be corrected according to an thermoacoustic data adjustment.

For example, as will be appreciated, thermoacoustic signals propagate through space in the form of acoustic pressure waves. Received signals at the ultrasound transducer array can be expressed according to equation 12:

$$p_s(t) = \int_S p(\vec{r}, t) \, dS \tag{12}$$

where S is the surface area of the ultrasound transducer array. Both the properties of the ultrasound transducer array and its positioning relative to the subject change the characteristics of the thermoacoustic data. The thermoacoustic signal strength received by the ultrasound transducer array is affected by various factors that are not related to signal generation, but rather associated with acoustic propagation. These factors depend on transducer spatial sensitivity, relative positioning between the ultrasound transducer array and the boundary between the object of interest and the reference, and the relative shape of the reference with respect to the ultrasound transducer array surface. Even for the same subject and the same ultrasound transducer array, changing the position and angle of the ultrasound transducer array during thermoacoustic data acquisition results in different measurements.

In an embodiment, a compensation factor is calculated based on information and measurements provided by the user or estimated using ultrasound image data. The compensation factor may be a single factor or multiple factors, where each factor is calculated information such as size and shape of the reference and the angle between the ultrasound transducer array and the boundary. In one embodiment, the compensation factors are calculated based on theoretical methods such as by using acoustic propagation and ultrasound transducer properties. In another embodiment, the compensation factors may be obtained from phantom and clinical studies. In yet another embodiment, both theoretical and experimental methods may be used.

When the thermoacoustic data is adjusted with the compensator factor, the thermoacoustic signal strength, $S_1$, in equation 11 should be replaced by the adjusted thermoacoustic signal strength, $\overline{S}_1$:

$$\kappa_{obj} \equiv \Gamma_{obj}\varepsilon''_{r,obj} = \frac{\overline{S}_l}{\omega\varepsilon_0 E_0^2 e^{-2\eta_{ref} d_{ref}}} + \Gamma_{ref}\varepsilon_0\varepsilon''_{r,ref} \tag{13}$$

In one embodiment, when the object is large enough to ignore partial volume effect, only the angle based adjustment is required. When the tangent vector of the object at the boundary of interest and the transducer's line of sight is not perpendicular, signal adjustment should be made to the acquired measurement. This adjustment can be written as follows:

$$S_1 = S_1 C(\theta) \tag{14}$$

where C is an angle based adjustment factor, θ is the angle between the tangent vector of the liver at the boundary and the transducer's line of sight.

Figure 10:
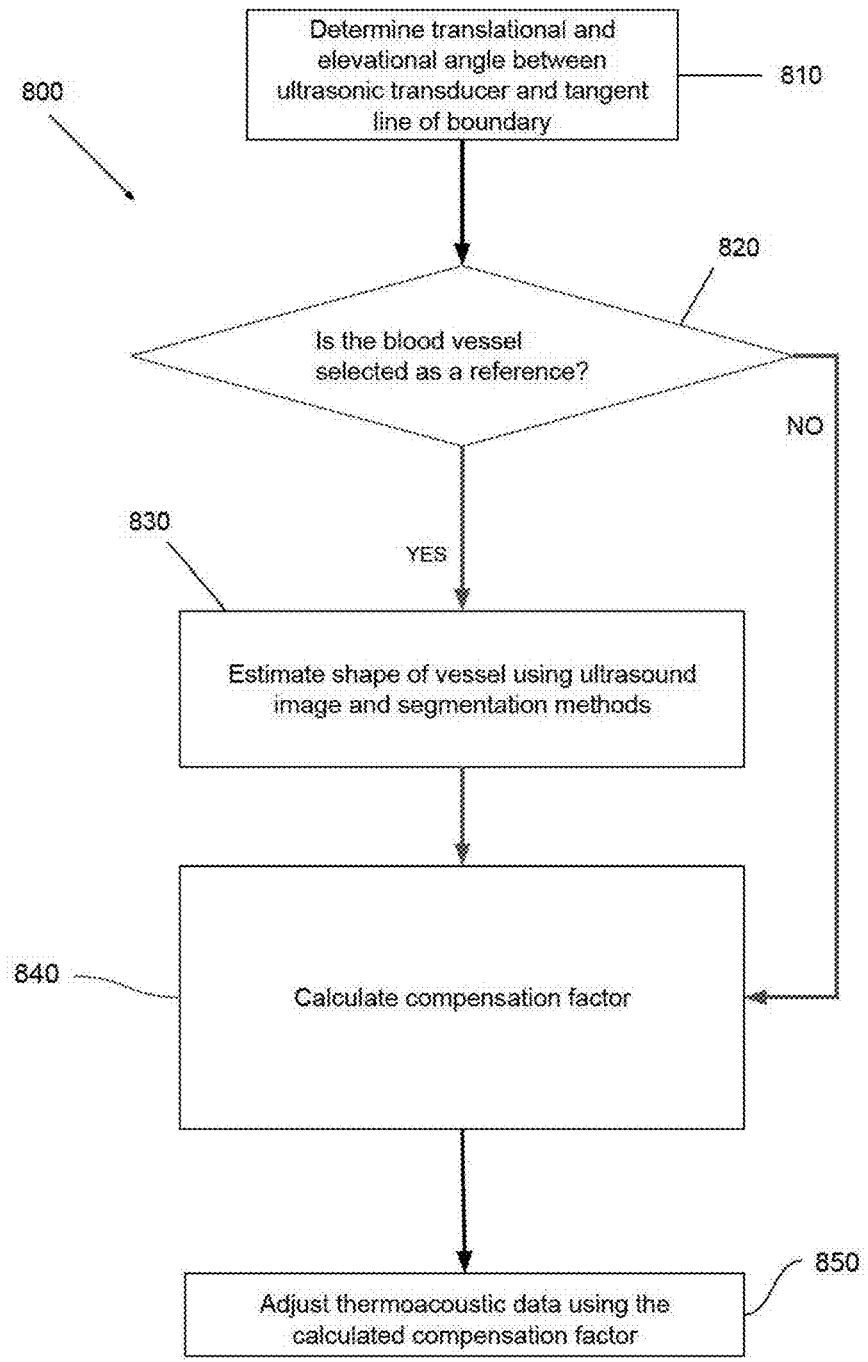
FIG. 10 is a flowchart of another thermoacoustic data adjustment.

An exemplary thermoacoustic data adjustment 800 is shown in FIG. 10. The translational and elevational angle between the ultrasound transducer array and the tangent line of the boundary is determined (step 810). A check is performed to determine if a reference is a blood vessel (step 820). If a reference is a blood vessel, the shape of the blood vessel is estimated by the computing device using ultrasound image data and segmentation methods (step 830) and the method continues to step 840. As will be appreciated, the shape of the blood vessel may be the thickness of the blood vessel, the length of the blood vessel within the field of view, and the cross section of the blood vessel. If the reference is not a blood vessel, the method does not perform step 830 and continues to step 840. During step 840, a compensation factor is calculated using information obtained in steps 810 to 830 and using the ultrasound transducer array characteristics. In this embodiment, the information that is used to calculate the compensation factor is at least one of the translational angle, the elevational angle, the thickness of the blood vessel (if selected as the reference), and spatial sensitivity of the ultrasound transducer array. Accordingly, the compensation factor is calculated. Thermoacoustic data obtained in step 403 is adjusted using the calculated compensation factor from step 840. Then, step 404 is executed.

Figure 11A:
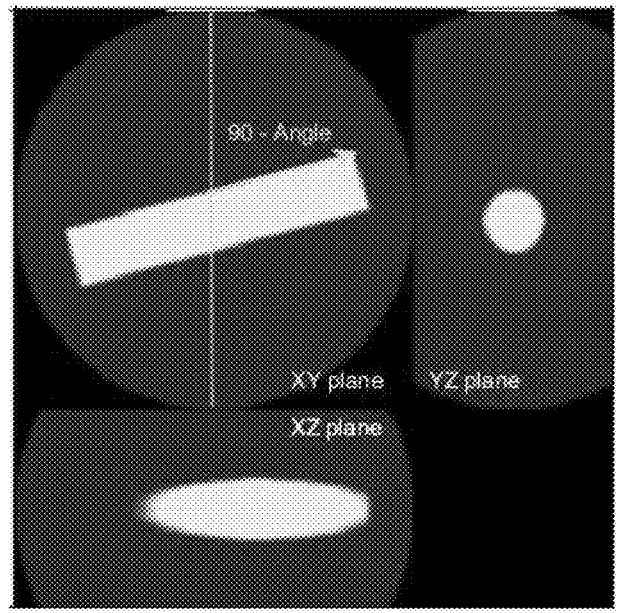
FIGS. 11a and 11b show an embodiment using a compensation factor.
Figure 11B:
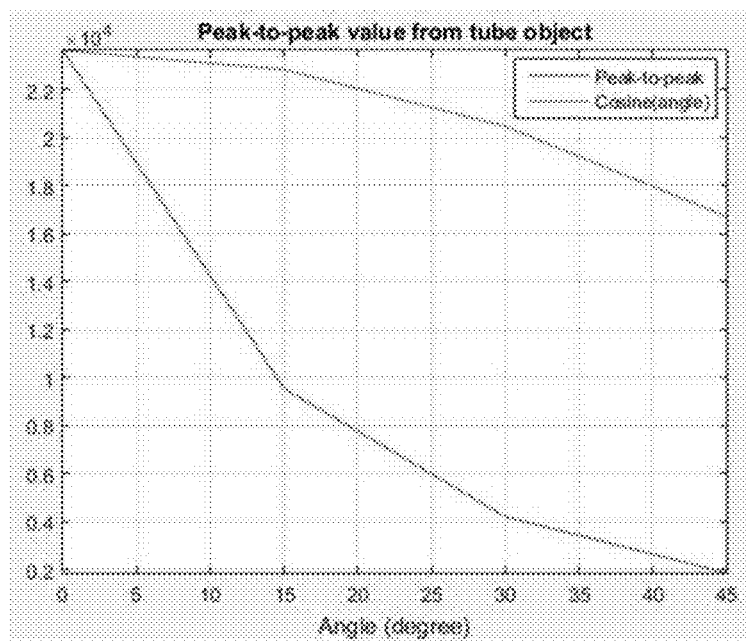

An embodiment where a compensation factor is used is shown in FIGS. 11a and 11b. As can be seen, when the angle between the ultrasound transducer array and a tangent line of the boundary is not a right angle, the thermoacoustic signal decreases as a function of the deviation from the right angle. As such, a compensation factor may be used to correct for the fact that the angle between the ultrasound transducer array and the tangent line of the boundary is not a right angle.

Figure 12A:
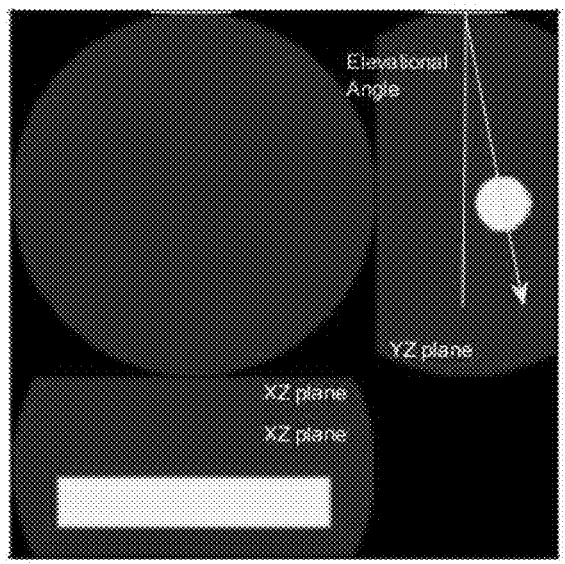
FIGS. 12a and 12b show another embodiment using a compensation factor.
Figure 12B:
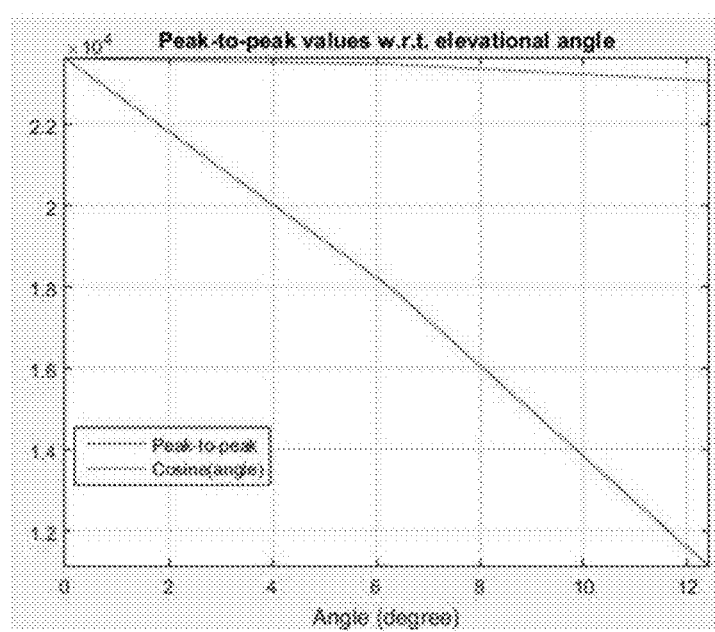

Another embodiment where a compensation factor is used is shown in FIGS. 12a and 12b. As can be seen, when a blood vessel is selected as the reference, the thermoacoustic signal decreases as a function of the elevational angle, which is defined as the angle between the displaying scanning plane and the scanning plane passing through the center of the blood vessel. As such, a compensation factor may be used to correct for the fact that the elevation angle does not pass through the center of the blood vessel.

Figure 13A:
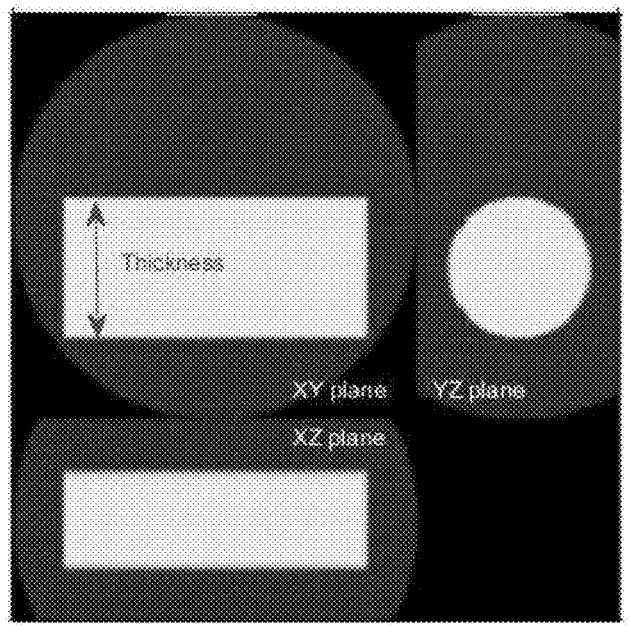
FIGS. 13a and 13b show another embodiment using a compensation factor.
Figure 13B:
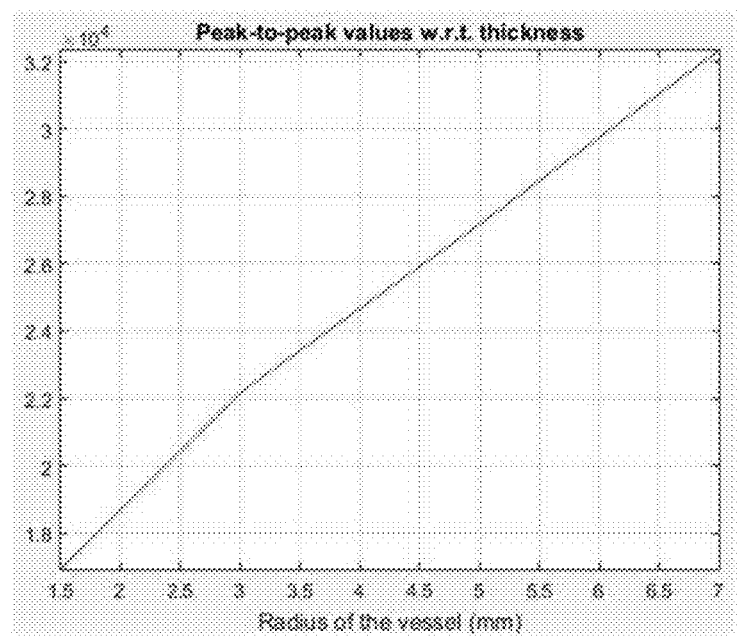

Another embodiment where a compensation factor is used is shown in FIGS. 13a and 13b. As can be seen, when a blood vessel is selected as the reference, the thermoacoustic signal increases as a function of the thickness of the blood vessel. As such, a compensation factor may be used to correct for the thickness of the blood vessel.

Figure 14:
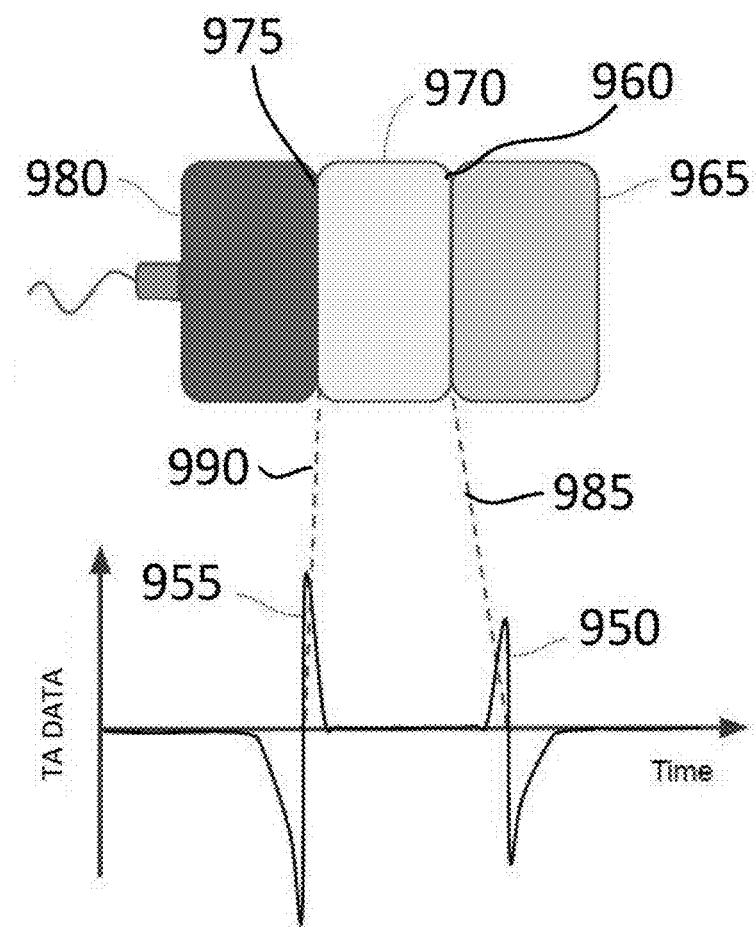
FIG. 14 is a graph showing exemplary bipolar signals obtained by the imaging system of FIG. 1 when an intermediate structure exists.

Although in embodiments described above the boundary is selected at a location where the object of interest and the reference are in close relation to one another, those skilled in the art will appreciate that alternatives are available. For example, in another embodiment an intermediate structure may be in between the reference and the object of interest. Exemplary bipolar signals 950 and 955 of this embodiment are shown in FIG. 14. The bipolar signals 950 and 955 represent thermoacoustic data obtained at a boundary 960 between reference 965 and intermediate structure 970 and a boundary 975 between intermediate structure 970 and object of interest 980, respectively. The dashed line 985 indicates a time point corresponding to the boundary 960 and dashed line 990 indicates a time point corresponding to the boundary 975.

Figure 15:
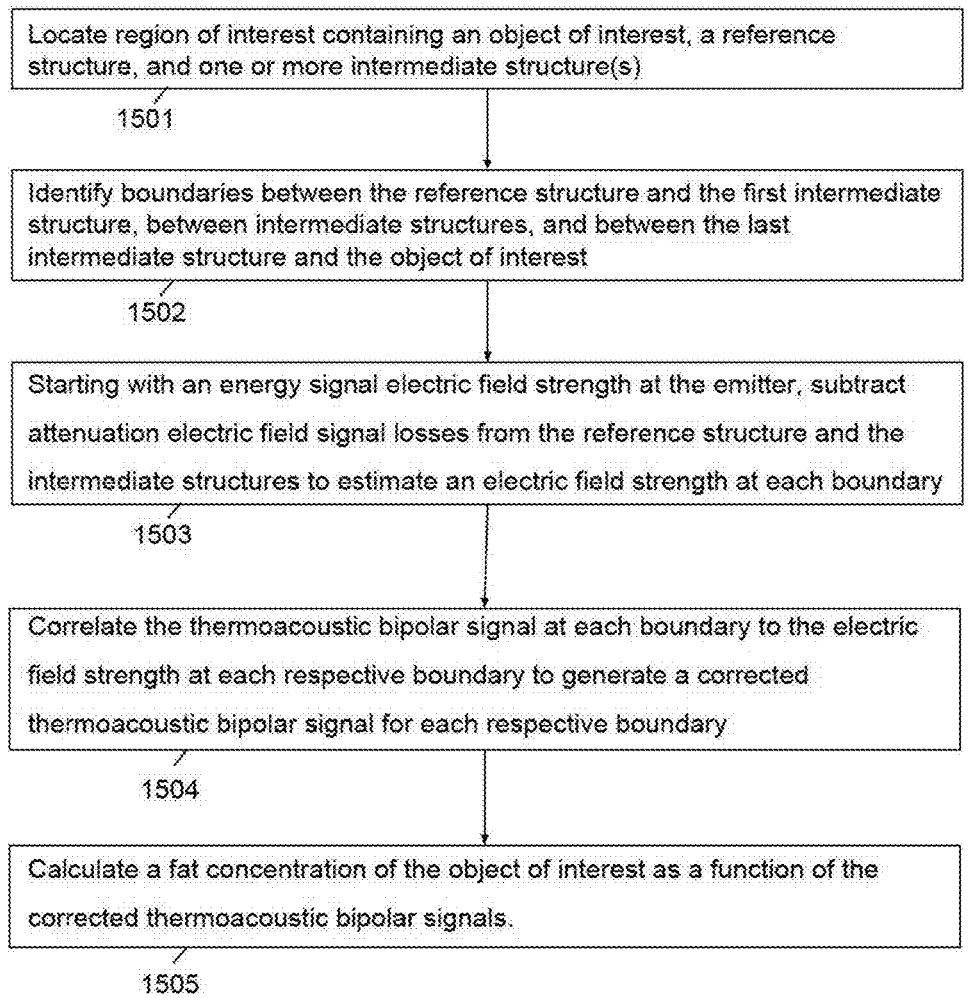
FIG. 15 is a flowchart showing another embodiment of steps for estimating the fractional fat content of an object of interest.

FIG. 15 shows an embodiment with one or more intermediate structures. Shown are step 1501, locate region of interest containing an object of interest, a reference structure, and one or more intermediate structure(s): step 1502, identify boundaries between the reference structure and the first intermediate structure, between intermediate structures, and between the last intermediate structure and the object of interest; step 1503, starting with an energy signal electric field strength at the emitter, subtract attenuation electric field signal losses from the reference structure and the intermediate structures to estimate an electric field strength at each boundary; step 1604, correlate the thermoacoustic bipolar signal at each boundary to the electric field strength at each respective boundary to generate a corrected thermoacoustic bipolar signal for each respective boundary; and step 1505, calculate a fat concentration of the object of interest as a function of the corrected thermoacoustic bipolar signals.

Although in embodiments described above the reference is described as being selected by the operator, those skilled in the art will appreciate that alternatives are available. For example, in another embodiment the reference may be automatically defined using an algorithm performed by the computing device 22 based on known geometry and/or known ultrasound properties of particular types of tissue within the region of interest. Further, the boundary between the reference and the object of interest may be automatically defined using algorithms based on ultrasound segmentation or thermoacoustic data analysis. As will be appreciated, both operator-defined and automatic methods may be combined.

Although in embodiments above the one or more ultrasound transducer arrays are described as being disconnectable from the ultrasound imaging system 24 and reconnectable to the thermoacoustic imaging system 26, those skilled in the art will appreciate that alternatives are possible. For example, the ultrasound imaging system 24 and the thermoacoustic imaging system 26 may have their own respective one or more transducer arrays. In another embodiment, the one or more ultrasound transducer arrays may be connected to a hub which itself is connected to the ultrasound imaging system and the thermoacoustic imaging system. In this embodiment, the hub may be controlled by the computing device 22 or by other input to switch operation between the ultrasound imaging system and the thermoacoustic imaging system and vice versa.

Although in embodiments described above a metric used is the difference between two peaks of a bimodal signal, those skilled in the art will appreciate that the metric may be a simple peak (maximum), a p-norm, area under the bimodal signal, etc.

As will be appreciated, embodiments of image processing described above can be performed on ultrasound and thermoacoustic images in real-time or off-line using images stored in memory.

Although the thermoacoustic imaging system is described as comprising an RF source configured to generate short pulses of RF electromagnetic radiation, those skilled in the art will appreciate that in other embodiments the thermoacoustic imaging system may comprise a visible light source or an infrared radiation source with a wavelength between 400 nm and 10 μm and a pulse duration between 10 picoseconds and 10 microseconds.

Although in embodiments described above the thermoacoustic imaging system and the ultrasound imaging system are described as using one or more ultrasound transducer arrays, those skilled in the art will appreciate that the alternatives are available. For example, a single transducer element, an ultrasound transducer array having a linear or curved one-dimensional array, or a two-dimensional ultrasound transducer array may be used. In addition, a gel-like material or water capsule may be used to interface the one or more ultrasound transducer arrays with the region of interest.

Although in embodiments described above, the fractional fat content of the object of interest is estimated using thermoacoustic data obtained of a single region of interest, those skilled in the art will appreciate that multiple regions of interest may be analyzed and combined.

Although in embodiments described above blood vessels are described as being identified manually by an operator, those skilled in the art will appreciate that blood vessels may be identified in other ways. For example, in another embodiment automatic or semi-automatic algorithms may be used to identify one or more blood vessels. In other embodiments, Doppler imaging methods may be used to identify blood vessels.

Those skilled in the art will appreciate that the above-described ultrasound image data and thermoacoustic data may be one-dimensional, two-dimensional or three-dimensional. In embodiments, the ultrasound image data may be in a different dimension than the thermoacoustic data. For example, ultrasound image data may be two-dimensional and the thermoacoustic data may be one-dimensional. Further, different fields of view may be used.

In another embodiment, different types or models of transducer arrays may be used with the thermoacoustic and ultrasound imaging systems. In this embodiment, a transform may be used to map a thermoacoustic absorption image to the ultrasound image. In another embodiment, in the event that knowledge of transducer array geometry is not readily available, the thermoacoustic absorption image may be mapped to the ultrasound image using phantom reference points. In this embodiment, a transform may be used to map known phantom reference points from the thermoacoustic absorption image to the phantom reference points on the ultrasound image.

Although the ultrasound imaging system is described as using B-mode ultrasound imaging techniques, other techniques may be used such as for example power Doppler images, continuous wave Doppler images, etc.

Figure 6:
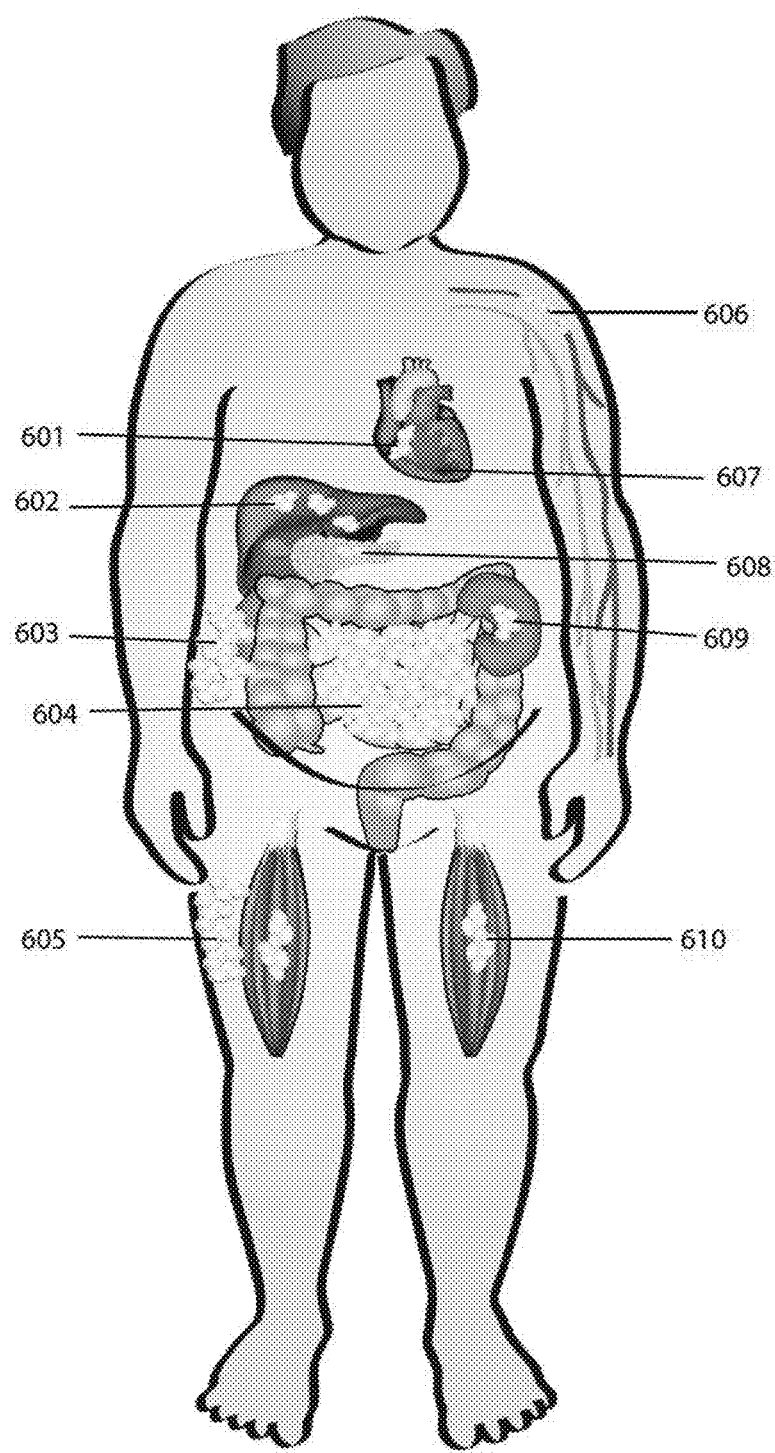
FIG. 6 is a diagram showing different locations in the human body where fat concentrations can be calculated.

FIG. 6 is a diagram showing different locations in the human body where fat concentrations can be calculated with the method and system provided in this disclosure. Shown are epi/pericardial adipose tissue 601, liver fat 602, subcutaneous adipose tissue 603, visceral adipose tissue 604, subcutaneous gluteal-femoral adipose tissue 606, perivascular adipose tissue 606, myocardial fat 607, pancreas fat 608, renal sinus fat 609, and muscle fat 610.

Those skilled in the art will appreciate that other objects of interest may be evaluated and other references may be used such as for example the heart, kidney(s), lung, esophagus, thymus, breast, prostate, brain, muscle, nervous tissue, epithelial tissue, bladder, gallbladder, intestine, liver, pancreas, spleen, stomach, testes, ovaries, uterus, skin and adipose tissues.

Although in embodiments described above thermoacoustic data is obtained of the region of interest, those skilled in the art will appreciate that thermoacoustic data may be obtained for an area larger than the region of interest.

Using the foregoing specification, the invention may be implemented as a machine, process, or article of manufacture by using standard programming and/or engineering techniques to produce programming software, firmware, hardware or any combination thereof.

Any resulting program(s), having computer-readable instructions, may be stored within one or more computer-usable media such as memory devices or transmitting devices, thereby making a computer program product or article of manufacture according to the invention. As such, functionality may be imparted on a physical device as a computer program existent as instructions on any computer-readable medium such as on any memory device or in any transmitting device, that are to be executed by a processor.

Examples of memory devices include, hard disk drives, diskettes, optical disks, magnetic tape, semiconductor memories such as FLASH, RAM, ROM, PROMS, and the like. Examples of networks include, but are not limited to, the Internet, intranets, telephone/modem-based network communication, hard-wired/cabled communication network, cellular communication, radio wave communication, satellite communication, and other stationary or mobile network systems/communication links.

A machine embodying the invention may involve one or more processing systems including, for example, computer processing unit (CPU) or processor, memory/storage devices, communication links, communication/transmitting devices, servers, I/O devices, or any subcomponents or individual parts of one or more processing systems, including software, firmware, hardware, or any combination or subcombination thereof, which embody the invention as set forth in the claims.

Using the description provided herein, those skilled in the art will be readily able to combine software created as described with appropriate or special purpose computer hardware to create a computer system and/or computer subcomponents embodying the invention, and to create a computer system and/or computer subcomponents for carrying out the method of the invention.

Although embodiments have been described above with reference to the accompanying drawings, those of skill in the art will appreciate that variations and modifications may be made without departing from the scope thereof as defined by the appended claims.

What is claimed is:

1. A method for identifying fat content in a region of interest, the method comprising:
    directing an energy signal with an energy signal electric field strength toward the region of interest, wherein the region of interest has an object of interest, a reference, and a boundary between the object of interest and the reference;
    receiving a thermoacoustic bipolar signal from the boundary, wherein the thermoacoustic bipolar signal is induced by the energy signal;
    correlating the thermoacoustic bipolar signal to an electric field strength of the reference at the boundary to generate a corrected thermoacoustic bipolar signal at the boundary; and
    calculating a fat concentration of the object of interest as a function of the corrected thermoacoustic bipolar signal at the boundary.

2. The method of claim 1, wherein the thermoacoustic bipolar signal is received by one thermoacoustic or ultrasonic transducer.

3. The method of claim 1, wherein the reference electric field strength at the boundary is derived from the thermoacoustic bipolar signal and an attenuation coefficient of the reference.

4. The method of claim 1, wherein the reference is a subcutaneous fat.

5. The method of claim 4, further comprising estimating a thickness of the subcutaneous fat, immediately after the receiving step.

6. The method of claim 5, wherein the reference electric field strength at the boundary is a function of the estimated thickness of the subcutaneous fat and an attenuation coefficient of fat.

7. The method of claim 1, wherein the object of interest is a liver and the calculated fat concentration correlates to a hepatic steatosis condition.

8. The method of claim 1, wherein the energy signal is a radio-frequency pulse.

9. The method of claim 1, wherein the energy signal is a visible light.

10. The method of claim 1, wherein the energy signal is an infrared radiation.

11. An system configured to execute the method of claim 1, the system comprising:
    an energy emitter configured to direct an energy signal with an energy signal electric field strength toward the region of interest, wherein the region of interest has an object of interest, a reference, and a boundary between the object of interest and the reference;

a thermoacoustic or ultrasonic transducer configured to receive a thermoacoustic bipolar signal from the boundary, wherein the thermoacoustic bipolar signal is induced by the energy signal; and a machine configured to accept data from the energy emitter and thermoacoustic or ultrasonic transducer, correlate the thermoacoustic bipolar signal to an electric field strength of the reference at the boundary to generate a corrected thermoacoustic bipolar signal at the boundary, and calculate a fat concentration of the object of interest as a function of the corrected thermoacoustic bipolar signal at the boundary.

12. The system of claim 11, wherein the reference electric field strength at the boundary is derived from the thermoacoustic bipolar signal and an attenuation coefficient of the reference.

13. The system of claim 11, wherein the reference is a subcutaneous fat.

14. The system of claim 13, further comprising estimating a thickness of the subcutaneous fat, immediately after the receiving step.

15. The system of claim 14, wherein the reference electric field strength at the boundary is a function of the estimated thickness of the subcutaneous fat an attenuation coefficient of fat.

16. The system of claim 11, wherein the object of interest is a liver and the calculated fat concentration correlates to a hepatic steatosis condition.

17. The system of claim 11, wherein the energy signal is a radio-frequency pulse.

18. The system of claim 11, wherein the energy signal is a visible light.

19. The system of claim 11, wherein the energy signal is an infrared radiation.

* * * * *